(12) United States Patent
Bhowmick et al.

(10) Patent No.: US 12,364,499 B2
(45) Date of Patent: Jul. 22, 2025

(54) DEVICES, SYSTEMS, AND METHODS FOR TISSUE TRACTION

(71) Applicant: Boston Scientific Limited, Hamilton (BM)

(72) Inventors: Nabarun Bhowmick, Kolkata (IN); Deepak K. Sharma, Muzaffarnagar (IN); Subodh Morey, Ponda (IN); Shrikant V. Raut, Mumbai (IN); James J. Scutti, Norwell, MA (US); Lauren S. Lydecker, Millbury, MA (US); Barry Weitzner, Acton, MA (US); James Weldon, Newton, MA (US)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 675 days.

(21) Appl. No.: 17/539,925

(22) Filed: Dec. 1, 2021

(65) Prior Publication Data

US 2022/0202436 A1    Jun. 30, 2022

Related U.S. Application Data

(60) Provisional application No. 63/130,489, filed on Dec. 24, 2020.

(51) Int. Cl.
*A61B 17/32* (2006.01)
*A61B 17/00* (2006.01)

(52) U.S. Cl.
CPC ............. *A61B 17/320016* (2013.01); *A61B 2017/00269* (2013.01); *A61B 2017/00951* (2013.01)

(58) Field of Classification Search
CPC ...... A61B 17/0218; A61B 2017/00269; A61B 2017/00951
See application file for complete search history.

(56) References Cited

U.S. PATENT DOCUMENTS 4,621,619 A * 11/1986 Sharpe .................. A61B 17/02
128/DIG. 15
7,494,461 B2    2/2009 Wells et al.
(Continued)

FOREIGN PATENT DOCUMENTS

EP              3037044 A1 *  6/2016  ......... A61B 17/0218
WO     WO-2013143556 A1 * 10/2013  ............. A61B 17/34

OTHER PUBLICATIONS

"Snap Bracelets from Tape Measures—Bistable Structures," The Naked Scientists, 4 pages, Nov. 21, 2010.

*Primary Examiner* — Eduardo C Robert
*Assistant Examiner* — Anna V. Little
(74) *Attorney, Agent, or Firm* — Seager, Tufte & Wickhem, LLP

(57) ABSTRACT

An elongated tissue traction device adhered to target tissue and configured to lift the target tissue away from surrounding tissue. The tissue traction device may lift the target tissue as a surgical procedure is performed, such as resecting or cutting of the target tissue. The tissue traction device may be a bistable spring. The tissue traction device is in a first stable configuration when initially adhered to the target tissue. The tissue traction device may be shifted (e.g., actuated) into the second configuration, such as when the tissue is resected or cut around the target tissue to which the tissue traction device is adhered. In the second stable configuration, the tissue traction device curls and lifts the target tissue from the surrounding tissue.

18 Claims, 7 Drawing Sheets

(56) References Cited

U.S. PATENT DOCUMENTS

| | | |
|---|---|---|
| 8,062,311 B2 | 11/2011 | Litscher et al. |
| 8,080,021 B2 | 12/2011 | Griego |
| 2009/0187198 A1 | 7/2009 | Weitzner |
| 2009/0264709 A1* | 10/2009 | Blurton ................ A61B 17/085 |
| | | 600/206 |
| 2011/0051892 A1* | 3/2011 | Shafer .................... A61B 90/39 |
| | | 378/65 |
| 2013/0150703 A1* | 6/2013 | Buchalter .............. A61B 6/481 |
| | | 600/407 |
| 2016/0074062 A1* | 3/2016 | Krupnick ........... A61B 17/3403 |
| | | 606/130 |
| 2017/0209132 A1* | 7/2017 | Bhatt ................ A61B 17/0218 |
| 2018/0235592 A1* | 8/2018 | Kass ................. A61B 17/0218 |
| 2018/0279869 A1* | 10/2018 | Wales ................ A61B 17/0206 |

* cited by examiner

DEVICES, SYSTEMS, AND METHODS FOR TISSUE TRACTION

CROSS-REFERENCE TO RELATED APPLICATIONS

This application claims the benefit of priority under 35 U.S.C. § 119 to U.S. Provisional Application No. 63/130,489, filed Dec. 24, 2020, the disclosure of which is hereby incorporated herein by reference in its entirety for all purposes.

FIELD

The present disclosure relates generally to the field of devices, systems, and methods for applying traction to tissue.

BACKGROUND

Various endoscopic surgical procedures require maneuvering about various anatomical structures. Some procedures, such as endoscopic mucosal resection (EMR), Endoscopic Submucosal Dissection (ESD), Pre-Oral Endoscopic Myotomy (POEM), etc., allow for minimally invasive endoscopic removal of benign and early malignant lesions, such as in the gastrointestinal (GI) tract. Because such procedures are minimally invasive, there is limited space to maneuver within the body. In such procedures involving cutting of tissue, the loose section of tissue may obstruct visibility, such as by falling on the endo scope, occluding visibility of the camera and creating a hindrance affecting movement of the instruments used during the procedure, and in reaching the extreme corners of the target tissue being cut. Various solutions for lifting the hanging mass of tissue, thus clearing the path for visibility and operation of medical tools and devices, have been developed. However, positioning of the elements used with such solutions may be challenging, particularly in a space-restricted environment. Also, the elements used with such solutions may require separate medical tools than those used to perform the procedure, and such tools may even require a separate working channel in the endoscope, thereby potentially increasing the size and/or complexity of the endoscope. Alternative solutions for lifting tissue during a procedure which reduce cost, complexity, and cognitive load presented by currently available solutions would be welcome.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a tissue traction device has an elongated body extending along a longitudinal axis with a first surface on a first side defined by a length along the longitudinal axis and a width transverse to the longitudinal axis, and a second surface on a second side opposite the first side and defined by the length and width. An anti-migration feature, such as a material securing element (e.g., a coating, such as a chemical with desired properties, such as a medical grade biocompatible adhesive), or a mechanical securing element (e.g., structural element sized, shaped, configured, dimensioned, and oriented to grip, grasp, anchor, engage, etc., on a larger structural scale) is provided on at least a portion of the first surface of the elongated body. The elongated body is a bistable spring with a first stable delivery configuration, and a second stable deployed configuration; in the first stable configuration of the elongated body; and in the second stable configuration of the elongated body, the elongated body pulls a surface with which the anti-migration feature is engaged as the elongated body curls along the length thereof. In some embodiments, in the first configuration the elongated body is curled along the width thereof with the first surface concave and the second surface convex. In some embodiments, the anti-migration feature is an adhesive, and the curved concave configuration of the first surface protects the adhesive from inadvertently adhering to a surface. In some embodiments, in the second configuration the elongated body is curled along the length thereof with the first surface convex and the second surface concave.

In some aspects, a tissue traction device has an elongated body extending along a longitudinal axis with a first surface on a first side defined by a length along the longitudinal axis and a width transverse to the longitudinal axis, and a second surface on a second side opposite the first side and defined by the length and width. A medical grade biocompatible adhesive is provided on at least a portion of the first surface of the elongated body. The elongated body is a bistable spring with a first stable delivery configuration, and a second stable deployed configuration; in the first stable configuration of the elongated body, the adhesive is protected from inadvertently adhering to a surface; and in the second stable configuration of the elongated body, the elongated body pulls a surface to which the adhesive is adhered as the elongated body curls along the length thereof. In some embodiments, in the first configuration the elongated body is curled along the width thereof with the first surface concave and the second surface convex. In some embodiments, the curved concave configuration of the first surface protects the adhesive from inadvertently adhering to a surface. In some embodiments, in the second configuration the elongated body is curled along the length thereof with the first surface convex and the second surface concave.

In some embodiments, the elongated body has first and second ends along the longitudinal axis, and the anti-migration feature (e.g., adhesive) on the first surface of the elongated body is limited to the first and second ends of the elongated body. Additionally or alternatively, at least one of the first and second ends of the elongated body is wider than a middle region of the elongated body extending between the first and second ends.

In some embodiments, the anti-migration feature is an adhesive provided on the entire first surface of the elongated body.

In some embodiments, the elongated body is formed of a flexible biocompatible metal foil.

In some embodiments, the anti-migration feature is an adhesive and the elongated body further includes an outer shell of biocompatible material formed over and not adhered to a spring biased element to form at least the first surface of the elongated body; a line of weakness is provided between a distal section and a proximal section of the outer shell; the adhesive is compatible with the material of the outer shell to remain adhered thereto; and grasping one of the distal or proximal section of the outer shell with the spring-biased element therein causes the grasped section of the outer shell to detach from the other section of the outer shell along the line of weakness to remove the grasped section of the outer shell along with the spring-biased element from the other section of the outer shell.

In some embodiments, the anti-migration feature is at least one of: an adhesive, an opening in the elongated body engaging tissue, tissue gripping elements formed from the elongated body along an opening in the elongated body and projecting therefrom, or one or more clips.

In accordance with various principles of the present disclosure, a tissue traction system is provided with an elongated body extending along a longitudinal axis and having a first surface on a first side defined by a length along the longitudinal axis and a width transverse to the longitudinal axis, and a second surface on a second side opposite the first side and defined by the length and width; and a delivery device having a lumen therethrough. An anti-migration feature is provided on at least a portion of the first surface. The tissue traction device is shiftable between a delivery configuration in which the elongated body fits within the delivery device lumen, and a deployed configuration in which the tissue traction device pulls a surface engaged by the anti-migration feature as the elongated body shifts from the delivery configuration to the deployed configuration. In some embodiments, in the delivery configuration the elongated body curls about the longitudinal axis to fit within the delivery device lumen. In some embodiments, the anti-migration feature is an adhesive, and in the delivery configuration the first surface is concave and shields the adhesive from contacting the delivery device lumen. In some embodiments, in the deployed configuration the elongated body curls along its length with the first surface convex to pull a surface engaged with the anti-migration feature.

In some aspects, a tissue traction system is provided with an elongated body extending along a longitudinal axis and having a first surface on a first side defined by a length along the longitudinal axis and a width transverse to the longitudinal axis, and a second surface on a second side opposite the first side and defined by the length and width; and a delivery device having a lumen therethrough. A medical grade biocompatible adhesive is provided on at least a portion of the first surface. The tissue traction device is shiftable between a delivery configuration in which the elongated body fits within the delivery device lumen, and a deployed configuration in which the tissue traction device pulls a surface adhered to the adhesive as the elongated body shifts from the delivery configuration to the deployed configuration. In some embodiments, in the delivery configuration the elongated body curls about the longitudinal axis to fit within the delivery device lumen. In some embodiments, in the delivery configuration with the first surface is concave and shields the adhesive from contacting the delivery device lumen. In some embodiments, in the deployed configuration the elongated body curls along its length with the first surface convex to pull a surface adhered to the adhesive.

In some embodiments, the system further includes an endoscope, with the delivery device extending through a working channel within the endoscope. In some embodiments, the tissue system further includes a pusher configured to extend through the delivery device lumen to push the tissue traction device out of the delivery device.

In some embodiments, the anti-migration feature is at least one of: an adhesive, an opening in the elongated body engaging tissue, tissue gripping elements formed from the elongated body along an opening in the elongated body and projecting therefrom, or one or more clips.

In some embodiments, the tissue traction device flares outwardly when no longer constrained within the delivery device lumen. Additionally or alternatively, in some embodiments, the anti-migration feature is an adhesive, and in the delivery configuration the first surface of the elongated body is concave and shields the adhesive from contacting the delivery device lumen.

In some embodiments, the elongated body has first and second ends along the longitudinal axis, and the anti-migration feature (e.g., adhesive) is provided on the first surface only at the first and second ends of the elongated body. Alternatively or additionally, at least one of the first and second ends of the elongated body is wider than a middle region of the elongated body extending between the first and second ends.

In some embodiments, the anti-migration feature is an adhesive provided on the entire first surface of the elongated body.

In some embodiments, the elongated body is formed of a flexible biocompatible metal foil.

In some embodiments, the anti-migration feature is an adhesive, and the elongated body further includes an outer shell of biocompatible material formed over and not adhered to a spring biased element to form at least the first surface of the elongated body; a line of weakness is provided between a distal section and a proximal section of the outer shell; the adhesive is compatible with the material of the outer shell to remain adhered thereto; and grasping one of the distal or proximal section of the outer shell with the spring-biased element therein causes the grasped section of the outer shell to detach from the other section of the outer shell along the line of weakness to remove the grasped section of the outer shell along with the spring-biased element from the other section of the outer shell.

In accordance with various principles of the present disclosure, a method of moving a region of target tissue away from surrounding tissue at the site of a surgical procedure includes engaging an anti-migration feature on a portion of an elongated flat tissue traction device in the form of a bistable spring to the region of target tissue when the tissue traction device is in a first stable configuration; and causing the tissue traction device to shift to a second stable configuration moving the region of target tissue away from surrounding tissue.

In some aspects, a method of moving a region of target tissue away from surrounding tissue at the site of a surgical procedure includes adhering a portion of an elongated flat tissue traction device in the form of a bistable spring to the region of target tissue when the tissue traction device is in a first stable configuration; and causing the tissue traction device to shift to a second stable configuration moving the region of target tissue away from surrounding tissue.

In some embodiments, the method further includes delivering the elongated tissue traction device through a delivery device in the first stable configuration curled within a lumen in the delivery device about the longitudinal axis of the elongated tissue traction device; pushing the distal end of the tissue traction device out of the delivery device and engaging the concave surface of the tissue traction device in the first stable configuration with tissue distal to the target tissue; and engaging the proximal end of the tissue traction device with the region of the target tissue.

In some embodiments, the method further includes applying a force to the tissue traction device to cause the tissue traction device to shift from the first stable configuration to the second configuration to pull the region of the target tissue away from surrounding tissue as the target tissue is resected or cut.

In some embodiments, the method further includes applying a force to the tissue traction device to cause the tissue traction device to shift from the first stable configuration to the second configuration to pull the region of the target tissue away from surrounding tissue as the target tissue is resected or cut.

In some embodiments, the method of engaging the anti-migration feature to the region of target tissue includes at least one of: adhering a portion of the elongated flat tissue traction device to the region of target tissue; engaging a region of target tissue with an opening in the elongated body engaging tissue; causing a region of target tissue to protrude through an opening in the elongated body to be engaged therein; engaging tissue gripping elements formed from the elongated body along an opening in the elongated body and projecting therefrom into a region of target tissue; or engaging a region of target tissue with one or more clips.

In some embodiments, the method of engaging the anti-migration feature to the region of target tissue includes at least one of: adhering a portion of the elongated flat tissue traction device to the region of target tissue; engaging a region of target tissue with an opening in the elongated flat tissue traction device; causing a region of target tissue to protrude through an opening in the elongated flat tissue traction device to be engaged therein; engaging tissue gripping elements formed from the elongated tissue traction device along an opening in the elongated flat tissue engaging device and projecting therefrom into a region of target tissue; or engaging a region of target tissue with one or more clips coupled to the elongated flat tissue retraction device.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
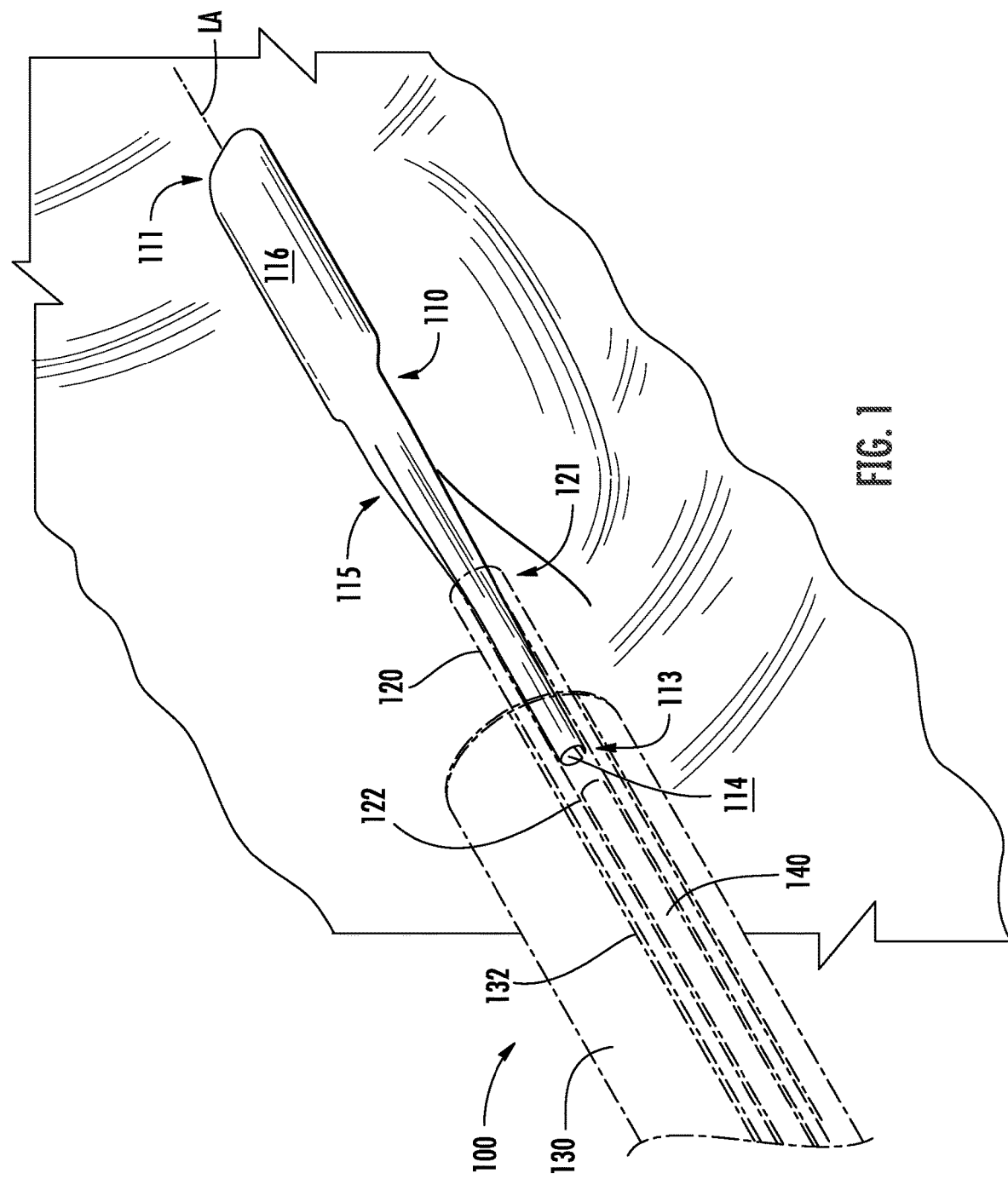
FIG. 1 is a perspective view of an example of an embodiment of a tissue traction system formed in accordance with various principles of the present disclosure, positioned near a schematic representation of a target tissue area to deploy a tissue traction device formed in accordance with various principles of the present disclosure.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted.

The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise, and including automated controller systems), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, a cavity, or a bore.

In accordance with various principles of the present disclosure, a tissue traction device is configured to be deployed with minimal manipulation of the tissue traction device and with minimal manipulation of tools or instruments to deploy the tissue traction device. In some embodiments, the tissue traction device has minimal moving parts. In some embodiments, the tissue traction device is formed of an elongated body shaped and configured to be coupled to tissue and to move the tissue, such as to retract the tissue, away from the site at which a procedure is being performed. The procedure may be a resection or dissection of tissue at a target area of tissue, and the tissue traction device may be positioned with respect to the target area to lift a portion of target tissue being resected or cut away from the remaining target tissue area. As used herein, the terms "target tissue" or "target area of tissue" or "target tissue area" may be used interchangeably herein to refer to an area or region of tissue on which a procedure is to be performed. In some instances, the target tissue is an unhealthy, diseased (i.e., cancerous, pre-cancerous etc.), or otherwise undesirable portion of tissue that may be healthy or unhealthy. A "target tissue" may also include tissues that are suspected of being unhealthy or diseased, but which require surgical removal for verification of their disease status by biopsy. It should be appreciated that surgical dissection of a "target tissue" typically includes removal of a portion of the surrounding healthy tissue along the "target tissue" margin to ensure complete removal and minimize the potential for metastasis of left behind or dislodged "target tissue" cells to other body locations. The target tissue area is within a treatment site in the body, such as the gastrointestinal system.

In accordance with various principles of the present disclosure, the shape or configuration of the tissue traction device need not be manipulated to engage tissue. Instead, the tissue traction device is simply placed on the target tissue and is coupled to/engages the target tissue upon placement. For instance, the tissue traction device may be coupled to a portion of the target tissue upon contact. In some embodiments, the tissue traction device presents a substantially smooth surface to the target tissue. In some embodiments, a medical grade adhesive is provided on a tissue-engaging surface on the tissue traction device. The adhesive may adhere the tissue traction device to the tissue on which the tissue traction device is placed or deployed upon contact, or with preferably minimal activation (e.g., heat activation). For instance, flexion of the distal tip of endoscope delivering the tissue traction device may provide sufficient force to ensure good contact of the tissue traction device with tissue to adhere thereto (e.g., target tissue). As such, the tissue traction device need not be manipulated by the medical professional (e.g., the medical professional need not take any steps to manipulate the shape or configuration of the tissue traction device) to cause the tissue traction device to be coupled to the target tissue.

In accordance with various principles of the present disclosure, the tissue traction device is shaped and/or configured to transition from a delivery configuration, in which the tissue traction device is delivered to the target area, to a deployed traction configuration in which the tissue traction device applies traction to a portion of target tissue. In some embodiments, the tissue traction device is formed from an elongated body configured as a bistable spring. The elongated body is delivered in a first stable configuration (e.g., a delivery configuration) and is actuatable, with minimal intervention, to move into a second stable configuration (e.g., a deployed configuration) in which the tissue traction device applies traction, such as to tissue at a target tissue area. The minimal intervention may be a simple contact with the tissue traction device. In some embodiments, the elongated body is substantially flat with a length significantly greater than a width, the length and width each being significantly greater than the thickness.

Various embodiments of tissue traction devices, and associated systems and methods of use will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

It will be appreciated that common features are identified by common reference elements and, for the sake of brevity and convenience, and without intent to limit, the descriptions of the common features are generally not repeated. For purposes of clarity, not all components having the same reference number are numbered. Moreover, a group of similar elements may be indicated by a number and letter, and reference may be made generally to one or such elements or such elements as a group by the number alone (without including the letters associated with each similar element). It will be appreciated that, in the following description, elements or components similar among the various illustrated embodiments are generally designated with the same reference numbers increased by a multiple of 100 and redundant description is generally omitted for the sake of brevity. Moreover, certain features in one embodiment may be used across different embodiments and are not necessarily individually labeled when appearing in different embodiments.

Figure 2:
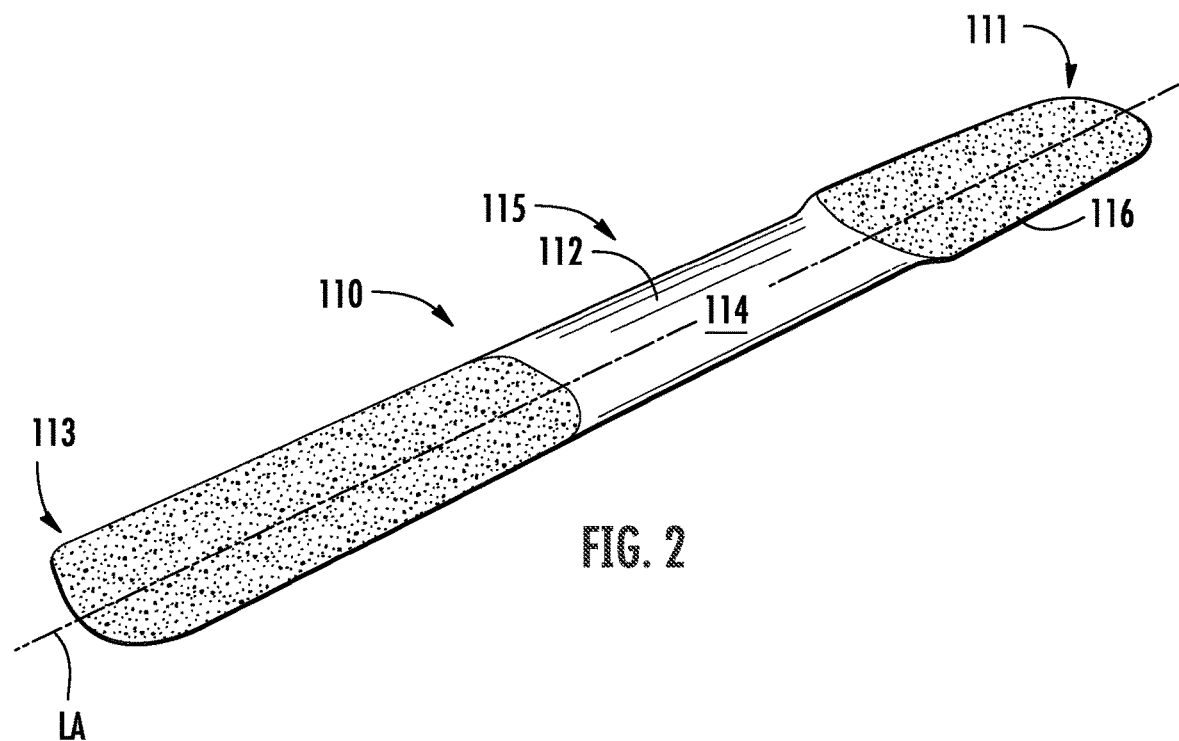
FIG. 2 is a perspective view of an example of an embodiment of a tissue traction device formed in accordance with principles of the present disclosure and in a first configuration.
Figure 3:
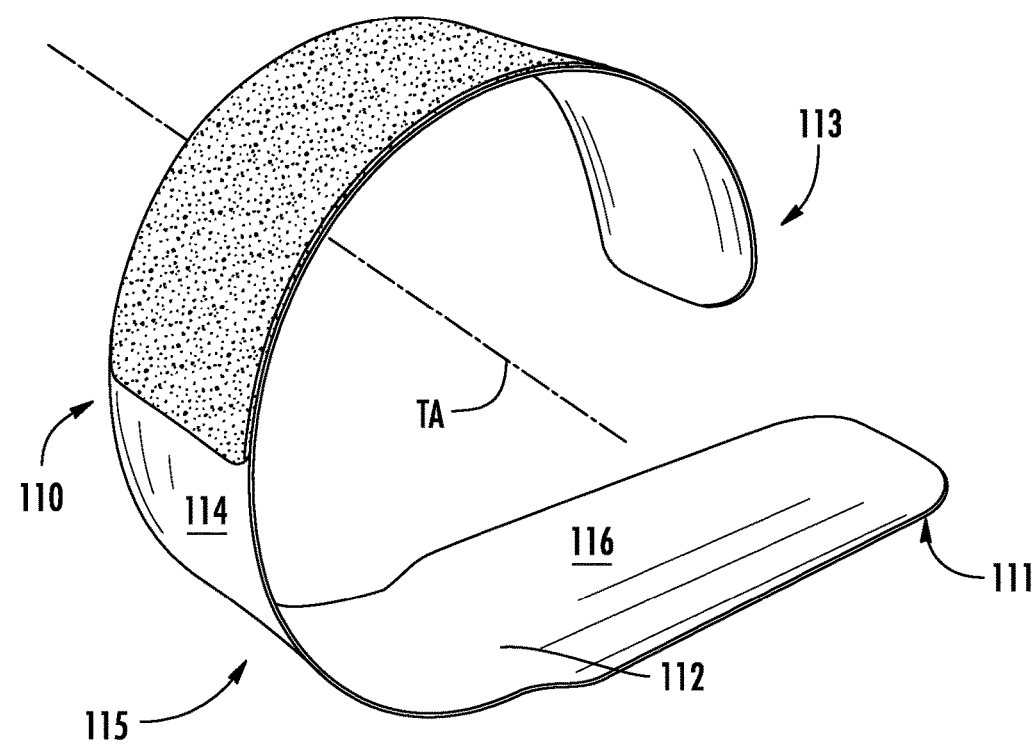
FIG. 3 is a perspective view of an example of an embodiment of a tissue traction device formed in accordance with principles of the present disclosure and in a second configuration.

Turning now to the drawings, a tissue traction system 100 is illustrated in FIG. 1 delivering an example of a tissue traction device 110 formed in accordance with various principles of the present disclosure to a target tissue TT at a treatment site TS. Although FIG. 1 illustrates a human gastrointestinal system as an example environment in which embodiments of the present disclosure may be applied or used or deployed, it will be appreciated that principles of the present disclosure may be applied beyond the gastrointestinal system. The illustrated tissue traction device 110 has an elongated body 112 formed of a flexible resilient biocompatible material, such as a superelastic metal such as nitinol or other superelastic material such as an ultra-high strength cobalt-chromium alloy such as MP35N or Elgiloy or Phynox or their variants, and may be in the form of a foil or thin sheet material. The elongated body 112 is formed to shift between a first configuration, such as illustrated in FIG. 2, and a second configuration, such as illustrated in FIG. 3. The elongated body 112 has a length along a longitudinal axis LA greater than its width (in a direction transverse to, such as perpendicular to, the longitudinal axis LA). In one embodiment, the elongated body 112 is formed from a thin sheet material with its length several times longer than its width. In some embodiments, the elongated body 112 can be pre-shaped into a compound-curled configuration which may be described by: (1) a pre-curved shape in which the curve is aligned along the length of the elongated body 112 (curved about the longitudinal axis LA); and (2) a partial loop curled about an axis transverse (preferably perpendicular) to the longitudinal axis LA. These two aspects of the pre-shaped elongated body 112 provide extremely strong curling forces when the elongated body 112 is constrained in a flattened state such as when it is loaded into a delivery system (as shown in FIG. 1). When the elongated body 112 is deployed from the delivery system, the strong curling forces are released and the elongated body 112 then transitions to the first configuration.

In FIG. 2, the elongated body 112 is illustrated in a first configuration, with the tissue traction device 110 is curled widthwise about its longitudinal axis LA (the axis extending along the longer dimension of the tissue traction device 110 between distal end 111 and a proximal end 113 of the elongated body 112). In the second configuration, as illustrated in FIG. 3, the tissue traction device 110 is curled lengthwise about an axis transverse to its longitudinal axis LA. In some embodiments, the tissue traction device 110 is a bistable spring, stable in either of the first or second configurations, and readily transitioning from one configuration to the other configuration by an activation input, such as application of a force or a change in temperature or other input. For example, when the tissue traction device 110 is in the first configuration, a first surface 114 of the elongated body 112 (defined by the length and width on one side of the elongated body 112) is concave and a second surface 116 of the elongated body 112 (defined by the length and width on the other, opposite side of the elongated body 112) is convex. It will be appreciated that the thickness (the distance between the first surface 114 and the second surface 116) is significantly less than either the length or the width of the elongated body 112 to allow such flexing of the elongated body 112. Application of minimal force (e.g., a light tap) to the concave first surface 114 causes the elongated body 112 to transition to the second configuration, causing the first surface 114 to become convex and the second surface 116 to become concave.

The tissue traction device 110 is illustrated in FIG. 1 in the first configuration, which may be alternately referenced herein as a delivery configuration, partially within a delivery device 120 (e.g., an elongated flexible tubular member, such as a catheter or sheath or the like, such terms being used interchangeably herein without intent to limit). The delivery device 120 may, in turn, be delivered through a working channel 132 of an additional delivery device 130, such as an endoscope. In the delivery configuration, the tissue traction device 110 may be curled about its longitudinal axis LA, which may be coincident with a longitudinal axis of the delivery device lumen 122 along which the tissue traction device 110 is delivered. A distal end 111 of the tissue traction device 110 is illustrated extending distally out of the distal end 121 of the delivery device 120. The delivery devices 120, 130 are illustrated in phantom so that the elongated body 112 may be seen in its curled configuration within a lumen 122 within the delivery device 120. In the illustrated example of an embodiment of a tissue traction device 110, the distal end 111 of the elongated body 112 may be wider than a middle region 115 of the elongated body 112. In some embodiments, the proximal end 113 of the elongated body 112 is also wider than the middle region 115 of the elongated body 112, and, in some embodiments, is substantially the same width as the distal end 111 of the elongated body 112. Examples of acceptable dimensions for an elongated body 112 suitable for use in accordance with various principles of the present disclosure include: an overall length of at least about 30 mm and at most about 60 mm (including increments of 0.5 mm therebetween), and a width of at least about 6 mm (including increments of 0.5 mm therebetween). If the distal end 111 and/or proximal end 113 is widened relative to a middle region 115 of the elongated body 112, the length of such widened end may be at least about 10 mm and at most about 15 mm (including increments of 0.5 mm therebetween), with the width of the widened end at most about 6 mm and the width of the middle region 115 at least about 2 mm.

In accordance with various principles of the present disclosure, a material (e.g., a coating, such as formed of a chemical with desired properties) may be provided on the tissue traction device 110 to facilitate securing (e.g., gripping, adhering, bonding, etc.) of the tissue traction device 110 to the target tissue TT upon deployment, and may be considered an anti-migration feature. For instance, a medical grade biocompatible adhesive (illustrated by shading in FIGS. 2, 3, and 5) may be provided on the first surface 114 of the tissue traction device 110 illustrated in FIG. 1 at least adjacent the distal end 111 and the proximal end 113 of the elongated body 112. Any of a variety of adhesives such as bioadhesives or adhesives using nanotechnologies may be used. Examples of suitable adhesives include, without limitation, a moisture-activated adhesive, such as a chitosan-based film that provides acute adhesion to the mucosal layer of the tissue when hydrated, and/or variants of chitosan modified with thiol, PEGdiamine and carboxymethylchitosan to improve adhesion and cohesion of the material. An additional adhesive may be provided on the first surface 114 of the tissue traction device 110 covered with a seal which breaks upon flexure of the tissue traction device 110 upon deployment. Such additional adhesive is exposed when the seal is broken to provide greater adhering capability to the tissue traction device 110 as the tissue traction device 110 flexes and lifts the target tissue TT therewith. Additionally or alternatively, a material configured and structure to have adhesive properties may be used. For instance, a material with draping adhesion may be used, such as inspired by the adhesive qualities of gecko feet. Such material may have dense fibers and/or projections and/or microfibers (e.g., on a nanoscale) which spread and grip tissue, such as by permitting temporary van der Waals forces which result from temporary polarization of molecules between the surfaces of the fibers/projections. Examples of such material includes, without limitation, GeckSkin™, described at https://geekskin.umass.edu/be. For the sake of convenience, reference is made generally to an "adhesive" to include any and all such materials which may be used as an anti-migration feature.

It will be appreciated that in addition to or instead of an adhesive, which may be considered a material securing element, a mechanical securing element may be used. A mechanical securing element in accordance with various principles of the present disclosure is a structural anti-migration feature configured to anchor the tissue traction device 110 to the target tissue TT. In contrast with a material securing element which adheres or bonds on a molecular level, a mechanical securing element is sized, shaped, configured, dimensioned, and oriented to grip, grasp, anchor, engage, etc., (such terms and other grammatical forms thereof being used interchangeably herein without intent to limit) on a larger structural scale. Various configurations of mechanical securing elements are known in the art and may be used advantageously in connection with a tissue traction device 110 as disclosed herein.

Figure 4:
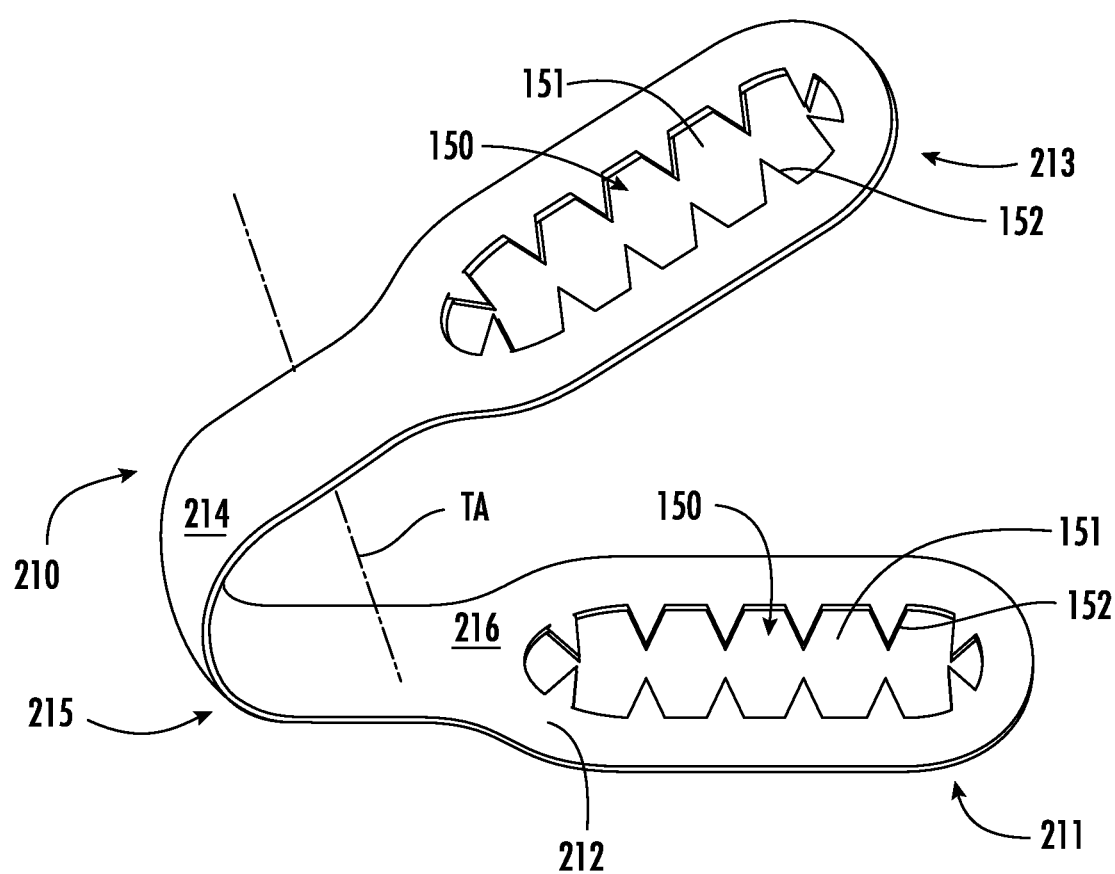
FIG. 4 is a perspective view of another example of an embodiment of a tissue traction device formed in accordance with principles of the present disclosure and in a second configuration.

An example of an embodiment of a tissue traction device 210 with a mechanical securing element 250 is illustrated in FIG. 4. The illustrated example of an embodiment of a mechanical securing element 250 is in the form of an opening 251 through at least one of the ends 211, 213 of the elongated body 212 of the tissue traction device 210. Upon deployment of the tissue traction device 210, tissue at the treatment site TS pushes up to protrude through the opening 251. A plurality of inwardly directed gripping elements 152 (e.g., teeth, barbs, protrusions, etc.) may be provided to engage the tissue and to grab, grasp, anchor into, etc., the tissue.

Figure 5:
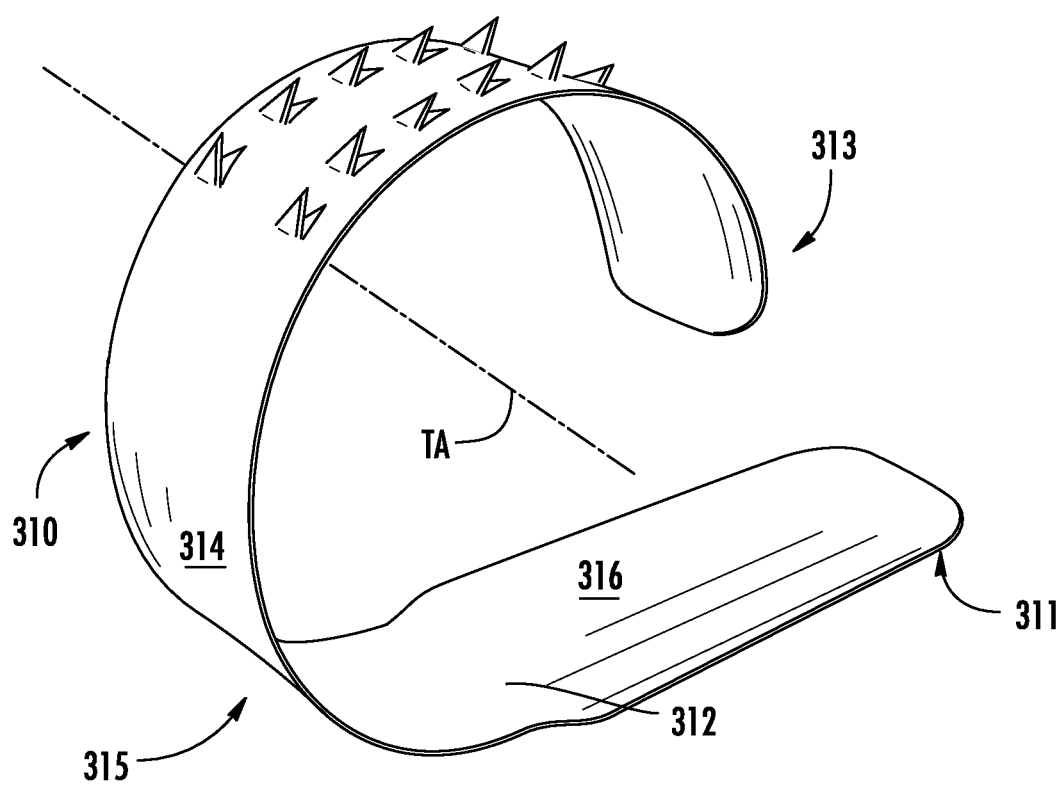
FIG. 5 is a perspective view of another example of an embodiment of a tissue traction device formed in accordance with principles of the present disclosure and in a second configuration.

Another example of an embodiment of a tissue traction device 310 with a mechanical securing element 350 is illustrated in FIG. 5. The illustrated example of an embodiment of a mechanical securing element 350 is in the form of one or more tissue-grasping features 352 formed from the elongated body 312 of the tissue traction device 310 such as by stamping, laser cutting, die-cutting, punching, etc., the material of the elongated body 312 in a desired shape. Upon curling into the second configuration as illustrated, the tissue-grasping features 352 project from the elongated body 312 of the tissue traction device 310. The tissue-grasping features 352 preferably are sized, shaped, configured, dimensioned, and oriented such that upon projecting from the elongated body 312 (e.g., from the second surface 316 towards the first surface 314) and towards the tissue at the treatment site TS, the tissue-grasping features 352 engage and grasp the tissue, thereby anchoring the tissue traction device 310 to the tissue.

Additionally or alternatively, a separately formed tissue fastener or clip or other mechanical securing device (e.g., a hemostatic clip), referenced herein as a clip for the sake of convenience and without intent to limit, may be used. In some embodiments, the clip is repositionable after being partially deployed. For example, the clip may be configured to allow for the clip to be releasably engaged (e.g., closed, but not locked into, engagement) with tissue when in a first configuration, and locked against opening out of engagement with tissue when in a second closed configuration. In some embodiments, the clip has jaws selectively movable away from each other to engage tissue therebetween, and movable towards each other to grasp the engaged tissue. The jaws may be hinged together (e.g., as a single piece), or separately formed and movable with respect to each other, such as by being pivotable about a pivot point. The jaws may have one or more additional grasping feature, such as a sawtooth or crenulated profile or teeth, at ends and/or along edges of the jaws. In some embodiments, the clip is movable with respect to the tissue traction device, even when coupled thereto. Movement, such as rotation (e.g., 360° rotation), of the clip may be controlled by a proximal control knob, dongle, or other actuator element. In some embodiments, the clip may be maneuvered, e.g., rotated, with one-to-one correspondence between movement of a control knob and the clip. In some embodiments, the clip is releasable from the delivery device such as by disrupting a frangible connection or overcoming a threshold pressure to separate a jointed (e.g., ball and yoke) connection. Examples of clips may include, but are not limited to, those described in U.S. Pat. No. 7,494,461, issued Feb. 24, 2009, and titled "Through The Scope Tension Member Release Clip"; U.S. Pat. No. 8,062,311, issued Nov. 22, 2011, and titled "Endoscopic Hemostatic Clipping Apparatus"; U.S. Pat. No. 8,080,021, issued Dec. 20, 2011, and titled "Multiple Clip Deployment Magazine"; and U.S. Patent Application Publication 2009/0187198, filed Dec. 15, 2008, and titled "Resolution Clip", all of which are herein incorporated by reference in their entirety and for all purposes.

The above-described material and/or structural securing elements may be considered, generically, to be anti-migration features. It will be appreciated that locations and extents of one anti-migration feature is generally applicable to another anti-migration feature. In some embodiments, the anti-migration feature configured to anchor the tissue traction device 110, 210, 310 to the target tissue TT is limited to the ends 111, 113, 211, 213, 311, 313 of the first surface 114, 214, 314, i.e., is provided only in the region of the ends 111, 113, 211, 213, 311, 313 of the elongated body 112, 212, 312 and not along the middle region 115, 215, 315 extending between the ends 111, 113, 211, 213, 311, 313. In some embodiments, an anti-migration feature may be provided along the middle region 115, 215, 315 of the elongated body 112, 212, 312 as well. If either or both of the distal end 111, 211, 311 and the proximal end 113, 213, 313 of the elongated body 112, 212, 312 are widened, the anti-migration feature is preferably at least provided on at least such widened end(s) of the elongated body 112, 212, 312.

In some embodiments, in the first configuration, the first surface 114 is concave with the elongated body 112 curled inwardly around the first surface 114 so that an anti-migration feature in the form of an adhesive on the first surface 114 is protected from contacting another surface, such as the interior of the delivery device 120. As such, the tissue traction device 110, carrying adhesive on the first surface 114 thereof, may be delivered to the target tissue area and pushed distally out of the distal end 121 of the delivery device 120 (e.g., with an elongated element such as a pusher 140, such as known or heretofore in the art) without adhering to the delivery device 120. Even as the elongated body 112 flares out widthwise from its curled configuration when no longer positioned (e.g., constrained) within the delivery device 120, the first surface 114 may still be somewhat concave so that the adhesive is somewhat distanced or shielded from inadvertently adhering to another surface. The elongated body 112 may advantageously be shifted (e.g., actuated) into the second configuration once at a desired location to better expose the adhesive to adhere to the desired location, as the first surface 114 is generally no longer convex when the elongated body 112 is in the second configuration.

Figure 7:
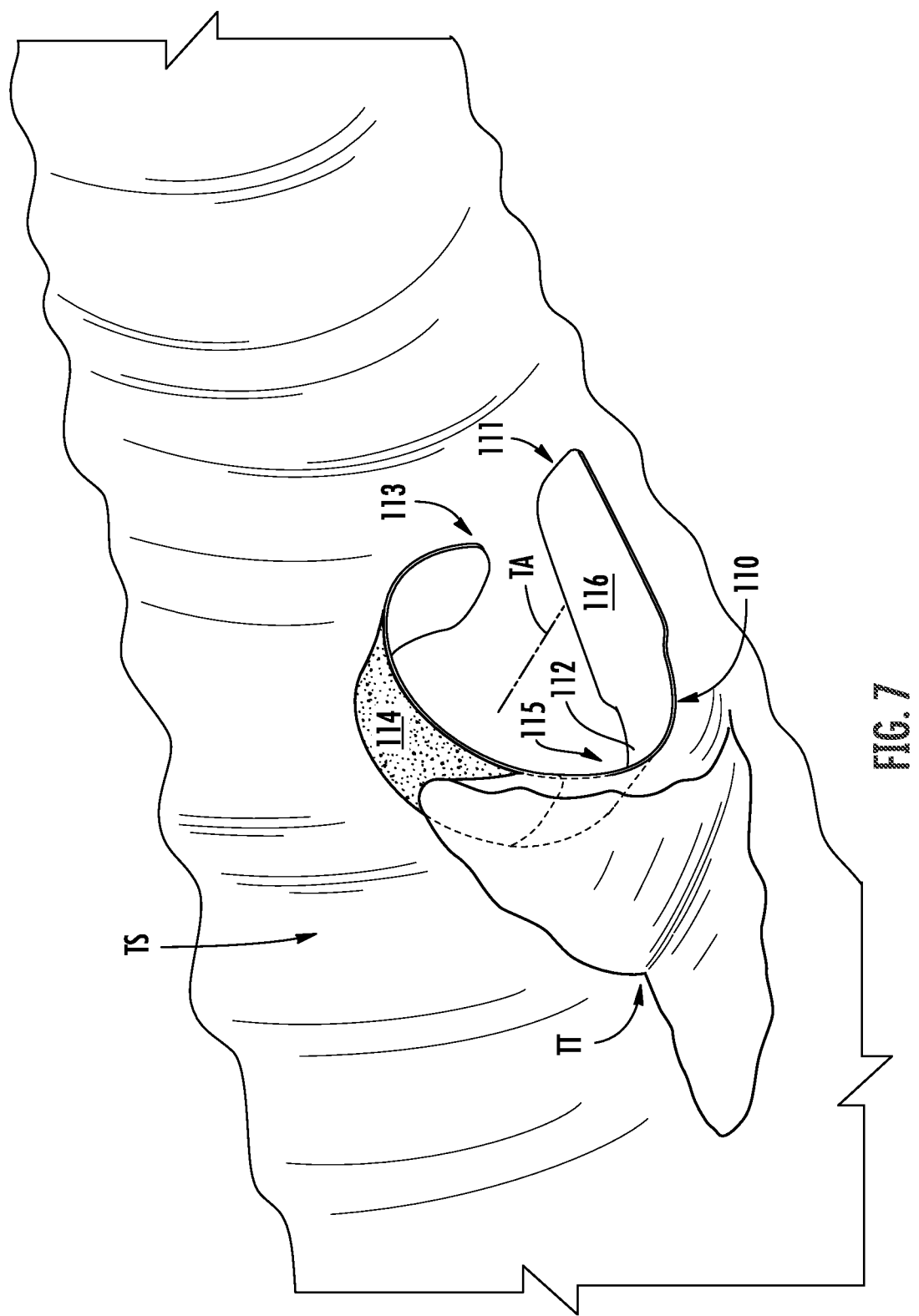
FIG. 7 is a proximal perspective view of a tissue traction device as in FIG. 1 and FIG. 2, moving into a second configuration to lift a section of target tissue at the treatment site.

In some embodiments, the elongated body 112 of a tissue traction device 110 such as described with reference to FIG. 2 and FIG. 3 is formed as a two-part device (providing additional benefits with respect to retrieval of the tissue traction device 110 as described in further detail below, with reference to FIG. 8), having an outer shell 160 and an inner spring-biased element 162. The outer shell 160 may be formed of a suitable biocompatible plastic material, such as a film, which encases the inner spring-biased element 162. In some embodiments, the outer shell 160 is formed of a suitable resilient material which can be shaped as described above into a compound-configuration (e.g., curled) having at least two stable configuration. For instance, a suitable resilient material would be sufficiently flexible to curl with the inner spring-biased element 162 and to be loaded into the delivery device 120 with the elongated body 112 in the above-described first configuration. Additionally or alternatively, a suitable material would be sufficiently flexible to accommodate the curled shape of the inner spring-biased element 162 as the extent/size of the tissue flap adhered to the elongated body 112 increases (e.g., as the surrounding tissue is resected or cut) and the elongated body 112 lifts the tissue flap (such as illustrated in FIG. 7 and described in further detail below). Concomitantly, the material of the outer shell 160 preferably is stiff enough to transfer the curling loads applied by the inner spring-biased element 162 to tissue adhered thereto. In some embodiments, the outer shell 160 material is selected to be compatible with the adhesive so that the adhesive remains adhered to the outer shell 160 and also to tissue at the treatment site TS to retain the tissue traction device 110 (including the inner spring-biased element 162) in place with respect to the tissue. Examples of suitable materials for the outer shell 160 include a metal construct made from nitinol sheet material with a polymer film or knitted fabric (made from polyethylene, polyurethane, ethylene vinyl alcohol copolymer, or other polymer material) over the tab area (where the adhesive is located). The tab area could be made from nitinol wire shaped into a loop, and welded to the nitinol sheet material, into which the inner spring-biased element 162 fits. Other examples of suitable materials for the outer shell 160 include a polymer cover material selected from one or more of the following or suitable substitutes therefor: polyether block amide (such as Pebax® or Vestamid®), thermoplastic copolyester (TPC) (such as Arnitel®), high density Polyethylene, polyester urethane, polyether urethane, polycarbonate urethane.

Deployment of a tissue traction device 110, 210, 310 as described above will be described for the sake of convenience with reference to the example of an embodiment of a tissue traction device 110 as illustrated in FIG. 2 and FIG. 3. Transition of the example of an embodiment of a tissue traction device 110 from the first configuration to the second configuration will now be described with sequential reference to FIG. 1, FIG. 6, and FIG. 7.

As described above, the tissue traction device 110 is delivered within the delivery device 120, such as within a lumen 122 defined within the delivery device 120, in a delivery configuration to a treatment site TS. As the tissue traction device 110 is being delivered, the entire elongated body 112 (both ends 111, 113) may be within the lumen 122 of the delivery device 120. Once the distal end 121 of the delivery device 120 is positioned near the target tissue area TT, the distal end 111 of the tissue traction device 110 is pushed out of the delivery device 120 (such as with a pusher) to be positioned for placement on the target tissue TT, such as near (distal to) a portion of the target tissue TT to be removed from the surrounding tissue at the treatment site TS. As may be appreciated, the elongated body 112 begins to flare outward upon exiting the delivery device lumen 122. In the illustrated embodiment, the tissue traction device 110 is a bistable spring and remains substantially straight and elongated (e.g., parallel to and extending along the longitudinal axis LA thereof) yet curled along its width (about its longitudinal axis LA). The delivery device 120 can be articulated and moved (such as via the additional delivery device 130) to move the distal end 111 of the tissue traction device 110 into position (e.g., at a position distal to the target tissue TT, such as on an unaffected area of tissue adjacent yet spaced apart from the target tissue TT), and to place the proximal end 113 of the tissue traction device 110 in contact with the target tissue TT.

Figure 6:
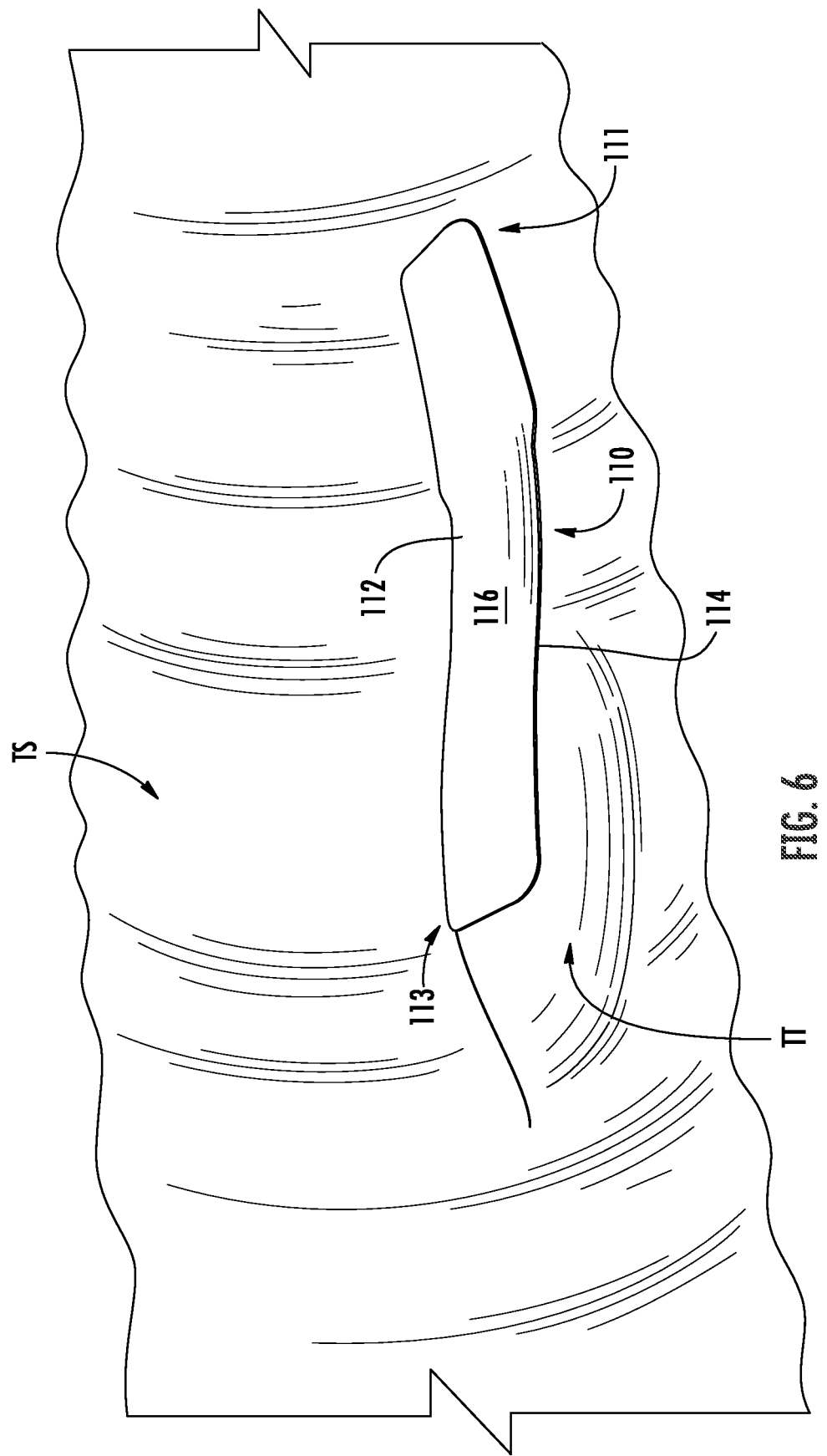
FIG. 6 is a perspective view of a tissue traction device as in FIG. 1, deployed at a treatment site.

As illustrated in FIG. 6, the delivery devices 120, 130 may be withdrawn proximally after the tissue traction device 110 has been placed on the target tissue TT. The adhesive on the first surface 114 of the elongated body 112 adheres the elongated body 112 to the target tissue TT. It will be appreciated that an alternative or additional mechanical anti-migration feature, such as described above and/or shown in the examples of embodiments illustrated in FIG. 6 and FIG. 7, will anchor to tissue at the treatment site TS as described above. The delivery device 120 may cross the target tissue TT and, upon retrieval (proximal withdrawal), the proximal end 111 of the tissue traction device 110 is placed on (e.g., falls on) the target tissue TT (e.g., a tumor area). Both ends 111, 113 of the tissue traction device 110 are thereby adhered in position at the treatment site TS. Upon release from a constrained position within the lumen 122 of the delivery device 120, the elongated body 112 is in a substantially straight configuration over the target tissue TT. However, a strong tension or curling force remaining in the elongated body 112 is released upon deployment of the tissue traction device 110, biasing the elongated body 112 towards its second configuration (e.g., curled as in FIG. 3) due to the tendency of the elongated body 112 to return back to its natural state.

As the target tissue TT (or a portion or region thereof) is resected or cut, the tissue traction device 110 may naturally begin to be reconfigured or transitioned into its second configuration, as illustrated in FIG. 7. As the resected or cut region of the target tissue TT separates from the surrounding tissue in the area of the target tissue TT, the force causing the elongated body 112 to transition (e.g., curl) naturally into its second configuration causes the proximal end 113 of the tissue traction device 110 to apply traction to the target tissue TT to which it is adhered. The resected or cut tissue which is adhered to the second surface 116 of the elongated body 112 along the proximal end 113 of the tissue traction device 110 is lifted away from the cutting tools, affording better visibility and approachability for the resection or cutting tools and for the medical professional to view the target tissue TT.

Figure 8:
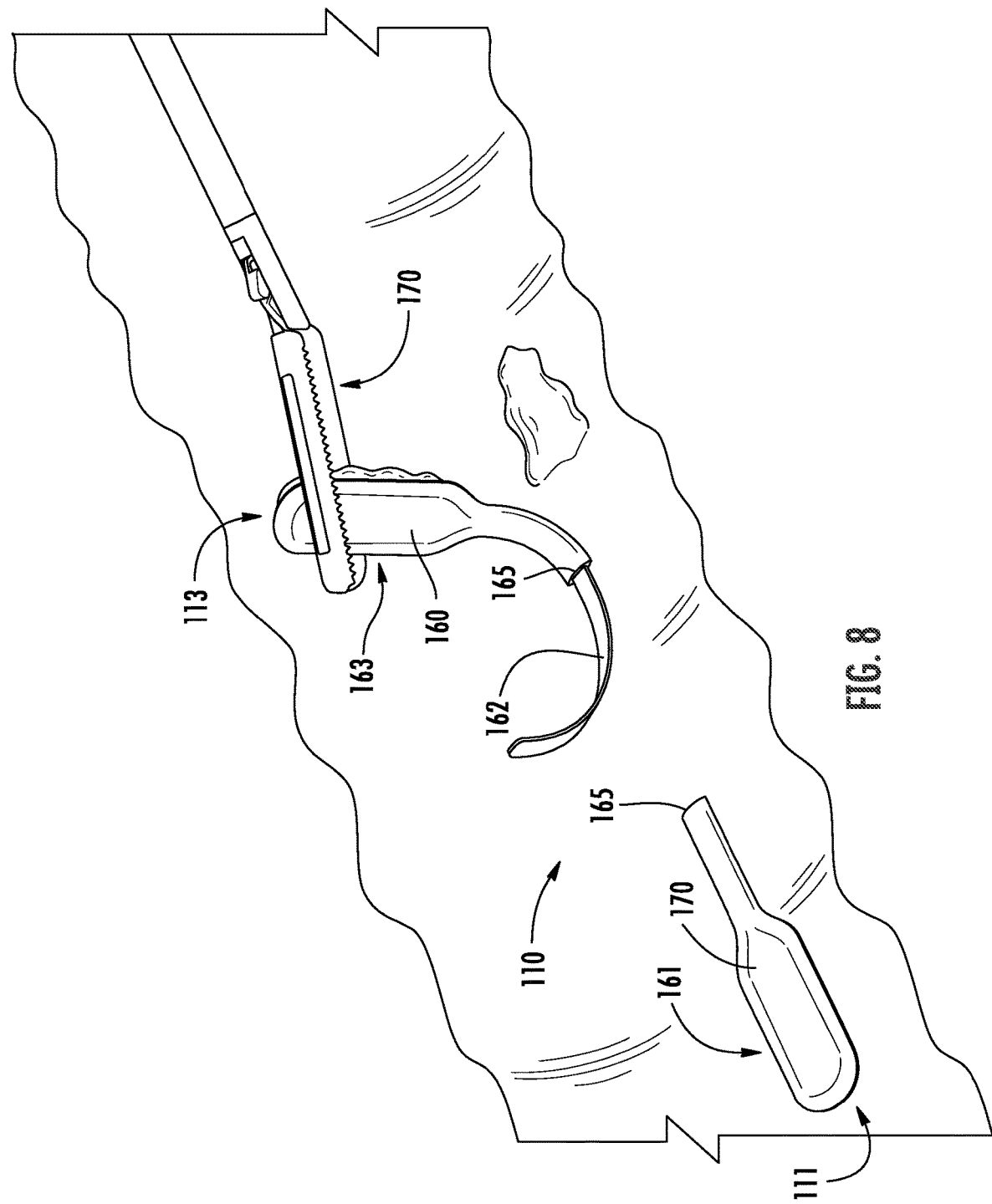
FIG. 8 is a distal perspective view of an embodiment of a tissue traction device as in FIG. 7, formed of an outer shell and inner spring-biased element, with a portion of the tissue traction device coupled to target tissue being retrieved from the treatment site.

In an embodiment in which the elongated body 112 of the tissue traction device 110 is formed of an outer shell 160, and an inner spring-biased element 162, the outer shell 160 may be separated into a distal section 161 (along the distal end 113 of the elongated body 112) and a proximal section 163 (along the proximal end 111 of the elongated body 112), such as along a line of weakness 165 (e.g., a perforation) to remove the target tissue TT adhered to the proximal section 163, as illustrated in FIG. 8. The elongated body 112 is placed with the line of weakness 165 distal to the portion of the target tissue TT to which the proximal end 113 of the elongated body 112 is adhered. Once the target tissue TT is sufficiently resected or cut and ready for removal, a grasper 170 (any device configured to grasp tissue as known or heretofore known in the art) may be used (e.g., passed through a lumen of the delivery device 120 and/or the additional delivery device 130) to grasp the proximal section of the outer shell 160 (along the proximal end 113 of the elongated body 112) along with the tissue adhered thereto (e.g., a tumor) to remove the tissue from the treatment site TS. Upon pulling the proximal section 163 proximally with the grasper 170, the outer shell 160 is broken along the line of weakness 165, so that the proximal section 163, along with target tissue TT adhered thereto, may be removed from the body by means of the grasper 170. The inner spring-biased element 162 may be encased within the outer shell 160 without being adhered thereto so that upon grasping a proximal section of the outer shell 160 with a proximal portion of the inner spring-biased element 162 therein, the entire inner spring-biased element 162 may be removed with the proximal portion of the outer shell 160. The distal section 161 may remain in place adhered to tissue. Because of its biocompatible nature, the portion of the elongated body 112 (outer shell 160) remaining within the body does not pose any harm to the body. Over time, the adhesive may lose effectiveness and the portion of the tissue traction device 11 left in the body may be flushed out, or tissue may grow over the portion of the tissue traction device 110.

Although the tissue traction device and use thereof is described with reference to a target tissue (e.g., a lesion in the gastrointestinal tract), other uses of a tissue traction device formed in accordance with principles of the present disclosure are within the scope and spirit of the present disclosure, and variations to the forms and configurations of the tissue traction device are within the scope and spirit of the principles of the present disclosure as well. The medical devices, instruments, tools, etc. of the present disclosure are not limited, and may include a variety of medical devices for accessing body passageways. For instance, a delivery device used herewith may be any suitable size, cross-sectional shape or area, and/or configuration permitting introduction and passage of medical instruments to the distal end of the delivery device. It is generally beneficial for the delivery device to be steerable, and the delivery device may have different areas of different flexibility or stiffness to promote steerability. The delivery device may include one or more working channels extending substantially longitudinally (axially) between the proximal end and the distal end of the delivery device. Examples of delivery devices suitable for use in accordance with various principles of the present disclosure include duodenoscopes, catheters, ureteroscopes, bronchoscopes, colonoscopes, arthroscopes, cystoscopes, hysteroscopes, and the like. The delivery devices and/or overtubes associated therewith may be made from any suitable biocompatible material known to one of ordinary skill in the art and having sufficient flexibility to traverse non-straight or tortuous anatomy. Such materials include, but are not limited to, rubber, silicon, synthetic plastic, stainless steel, metal-polymer composite; metal alloys of nickel, titanium, copper cobalt, vanadium, chromium, and iron; superelastic or shape memory material such as nitinol (nickel-titanium alloy); different layers of different materials and reinforcements. Such materials may be made of or coated with a polymeric or lubricious material to enable or facilitate passage of a deliver device therethrough. In some embodiments, the working channels may be made of or coated with a polymeric or lubricious material to facilitate passage of the introduced medical instrument(s) through the working channel(s).

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A tissue traction device comprising:
   an elongated body extending along a longitudinal axis and having a first end along the longitudinal axis, a second end along the longitudinal axis, a first surface on a first side defined by a length along the longitudinal axis and a width transverse to the longitudinal axis, and a second surface on a second side opposite the first side and defined by the length and width; and
   an adhesive provided on the first surface of the elongated body along at least the first end and the second end of the elongated body;
   wherein:
   the first end of the elongated body has a first end outer width transverse to the longitudinal axis from a first side edge of the first end to a second side edge of the first end opposite the first side edge of the first end;
   the second end of the elongated body has a second end outer width transverse to the longitudinal axis from a first side edge of the second end to a second side edge of the second end opposite the first side edge of the second end;
   a middle region of the elongated body extending from the first end to the second end of the elongated body has a middle region outer width transverse to the longitudinal axis from a first side edge of the middle region to a second side edge of the middle region opposite the first side edge of the middle region, the middle region outer width extending from the first end of the elongated body to the second end of the elongated body;
   the outer width of the first end of the elongated body and the outer width of the second end of the elongated body are wider than the outer width of the middle region of the elongated body;
   the elongated body is a bistable spring with a first stable configuration in which the elongated body is curled along the width thereof with the first surface concave and the second surface convex, and a second stable configuration in which the elongated body is curled along the length thereof with the first surface convex and the second surface concave;
   the adhesive engages tissue upon deployment of the elongated body at a deployment site to adhere the first end and the second end of the elongated body to tissue at the deployment site; and
   in the second stable configuration of the elongated body, the elongated body pulls a surface with which the adhesive is engaged as the elongated body curls along the length thereof.

2. The tissue traction device of claim 1, wherein the adhesive is limited to the first and second ends of the elongated body.

3. The tissue traction device of claim 1, wherein the adhesive is a bioadhesive or an adhesive using nanotechnology or a moisture-activated adhesive or an adhesive with draping adhesion.

4. The tissue traction device of claim 1, wherein the adhesive is covered with a seal which breaks upon flexure of the tissue traction device.

5. The tissue traction device of claim 1, wherein the adhesive is provided on the entire first surface of the elongated body.

6. The tissue traction device of claim 1, wherein the elongated body is formed of a flexible biocompatible metal foil.

7. The tissue traction device of claim 1, wherein:
   in the first stable configuration of the elongated body, the adhesive is protected from inadvertently adhering to a surface;
   the elongated body further comprises an outer shell of biocompatible material formed over and not adhered to a spring biased element to form at least the first surface of the elongated body;
   a line of weakness is provided between a distal section and a proximal section of the outer shell;
   the adhesive is compatible with the material of the outer shell to remain adhered thereto; and
   grasping one of the distal or proximal section of the outer shell with the spring-biased element therein causes the grasped section of the outer shell to detach from the other section of the outer shell along the line of weakness to remove the grasped section of the outer shell along with the spring-biased element from the other section of the outer shell.

8. A tissue traction system comprising:
a tissue traction device as recited in claim 1; and
a delivery device having a lumen therethrough;
wherein:
the tissue traction device is shiftable between a delivery configuration in which the elongated body fits within the delivery device lumen, and a deployed configuration in which the tissue traction device pulls a surface engaged with the adhesive as the elongated body shifts from the delivery configuration to the deployed configuration.

9. The tissue traction system of claim 8, further comprising an endoscope, the delivery device extending through a working channel within the endoscope.

10. The tissue traction system of claim 9, further comprising a pusher configured to extend through the delivery device lumen to push the tissue traction device out of the delivery device.

11. The tissue traction system of claim 9, wherein:
the elongated body further comprises an outer shell of biocompatible material formed over and not adhered to a spring biased element to form at least the first surface of the elongated body;
a line of weakness is provided between a distal section and a proximal section of the outer shell;
the adhesive is compatible with the material of the outer shell to remain adhered thereto; and
grasping one of the distal or proximal section of the outer shell with the spring-biased element therein causes the grasped section of the outer shell to detach from the other section of the outer shell along the line of weakness to remove the grasped section of the outer shell along with the spring-biased element from the other section of the outer shell.

12. The tissue traction system of claim 8, wherein:
in the delivery configuration the first surface of the elongated body is concave and shields the adhesive from contacting the delivery device lumen; and the tissue traction device flares outwardly when no longer constrained within the delivery device lumen.

13. The tissue traction system of claim 8, wherein the adhesive is provided on the first surface only at the first and second ends of the elongated body.

14. The tissue traction system of claim 8, wherein adhesive is provided on the entire first surface of the elongated body.

15. The tissue traction system of claim 8, wherein the elongated body is formed of a flexible biocompatible metal foil.

16. A method of moving a region of target tissue away from surrounding tissue at the site of a surgical procedure, the method comprising:
delivering the tissue traction device as recited in claim 1;
engaging the adhesive to the region of target tissue when the tissue traction device is in the first stable configuration; and
causing the tissue traction device to shift to the second stable configuration moving the region of target tissue away from surrounding tissue.

17. The method of claim 16, further comprising:
delivering the elongated tissue traction device through a delivery device in the first stable configuration curled within a lumen in the delivery device about the longitudinal axis of the elongated tissue traction device;
pushing the distal end of the tissue traction device out of the delivery device and engaging the concave surface of the tissue traction device in the first stable configuration to tissue distal to the target tissue; and
engaging the proximal end of the tissue traction device with the region of the target tissue.

18. The method of claim 17, further comprising applying a force to the tissue traction device to cause the tissue traction device to shift from the first stable configuration to the second configuration to pull the region of the target tissue away from surrounding tissue as the target tissue is cut.

* * * * *